(12) United States Patent
Rodriguez et al.

(10) Patent No.: US 6,435,013 B1
(45) Date of Patent: Aug. 20, 2002

(54) FERROMAGNETIC PARTICLE SENSOR

(75) Inventors: Lorenzo Guadalupe Rodriguez; Warren Baxter Nicholson, both of El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/933,242

(22) Filed: Aug. 20, 2001

(51) Int. Cl.[7] .................. G01N 11/00; G01N 29/00; G01N 15/06
(52) U.S. Cl. ............... 73/61.75; 73/53.01; 73/61.42
(58) Field of Search ................. 73/61.75, 53.01, 73/7, 53.05, 53.07, 61.42

(56) References Cited

U.S. PATENT DOCUMENTS 5,801,591 A  9/1998 Parrott .................. 331/96
5,869,748 A  2/1999 Stevenson et al. ......... 73/53.01
6,318,147 B1 11/2001 Steinruck et al. ............ 73/7

Primary Examiner—Thomas P. Noland
Assistant Examiner—Jay L Politzer
(74) Attorney, Agent, or Firm—Margaret A. Dobrowitsky

(57) ABSTRACT

A ferromagnetic particle sensor includes a housing having a first electromagnet and a second electromagnet attached to the interior surface thereof. A mass sensitive surface acoustic wave (SAW) sensor is disposed between the electromagnets. The sensor is submerged in lubricating fluid and as the electromagnets are energized they produce magnetic forces that draw fluid-borne ferromagnetic particles past the SAW sensor. The SAW sensor is used measure the mass of the ferromagnetic particles and determine when the volume of particles in the lubricating fluid increases.

2 Claims, 2 Drawing Sheets

FERROMAGNETIC PARTICLE SENSOR

TECHNICAL FIELD

The present invention relates generally to oil condition sensors.

BACKGROUND OF THE INVENTION

In order to protect an engine from damage, it is necessary to change the lubricating oil when it deteriorates. On board oil conditions sensors have been provided that measure oil condition parameters, e.g., conductivity, in order to determine if the oil can still provide the proper lubrication for the engine. Other parameters can be determined by taking a sample of the engine oil and testing it at a laboratory.

One such parameter is the quantity of wear metals in the engine oil. The wear metals are debris worn off internal engine parts caused by part-to-part contact. The most common of the wear metals is iron that is worn off of the pistons, cylinder walls, rings, valves, valve guides, gears, and bearings. The wear metals become oil-borne and the quantity of wear metals within the engine oil provide an indication of the condition of the oil. Specifically, as the quantity of wear metals in the oil increase, the condition of the oil worsens.

Typically, to determine the volume of wear metals in the engine oil, a sample is taken to a laboratory and the solids are separated from the oil. Then, the solids are burned in a plasma and the light from the burning solids is directed into a spectrometer. The wavelength and intensity of the light provides an indication as to the type and quantity of metal present in the oil sample. This method is an effective way to determine the wear metals present in the lubricating oil. However, it cannot be performed on board the vehicle. Moreover, it is expensive and the engine typically is taken out of service while the test is being performed.

The present invention has recognized these prior art drawbacks, and has provided the below-disclosed solutions to one or more of the prior art deficiencies.

SUMMARY OF THE INVENTION

A ferromagnetic particle sensor includes a hollow housing. A first electromagnet and a second electromagnet are supported by the housing. Moreover, a mass sensitive surface acoustic wave sensor is disposed vertically between the electromagnets.

In a preferred embodiment, the housing includes a base and the sensor further includes a circuit board extending from the base of the housing between the electromagnets. The mass sensitive acoustic wave sensor is attached to the circuit board. Preferably, the first electromagnet includes a coil wound around a core and the second electromagnet includes a coil wound around a core and the cores are made from a soft magnetic material.

In a preferred embodiment, the base is formed with external threads and the sensor is installed in a fluid reservoir that has a bore formed with correspondingly sized and shaped internal threads. Moreover, the reservoir defines an exterior surface and the base includes a flange that abuts the exterior surface of the reservoir when the sensor is installed therein. Also, in a preferred embodiment, the base includes an "O" ring groove that circumscribes the base and the sensor further comprises an "O" ring disposed therein. Preferably, the continuous sidewall is formed with one or more holes to allow oil to flow therethrough.

In another aspect of the present invention, a method for measuring ferromagnetic particles in lubricating fluid includes providing a first electromagnet and a second electromagnet. A mass sensitive surface acoustic wave sensor is disposed between the electromagnets. The electromagnets are selectively energized to attract ferromagnetic particles toward the mass sensitive surface acoustic wave sensor.

In yet another aspect of the present invention, a ferromagnetic particle sensor includes a hollow housing that defines an interior. Moreover, the sensor includes means for drawing ferromagnetic particles into the interior of the housing and means for sensing the mass of any ferromagnetic particles within the interior of the housing.

In another aspect of the present invention, a method for measuring ferromagnetic particles in lubricating fluid that has moving parts disposed therein includes providing a first electromagnet and a second electromagnet. A mass sensitive surface acoustic wave sensor is disposed between the electromagnets. The mass sensitive surface acoustic wave sensor includes a reference radio frequency amplifier that outputs a reference frequency and a sample radio frequency amplifier that outputs a sample frequency. In this aspect a difference frequency is determined based on the reference frequency and the sample frequency. Moreover, a wear rate of the parts disposed in the lubricating fluid is determined based on the difference frequency.

The present invention will now be described, by way of example, with reference to the accompanying drawings, in which:

DESCRIPTION OF AN EMBODIMENT OF THE INVENTION

Figure 1:
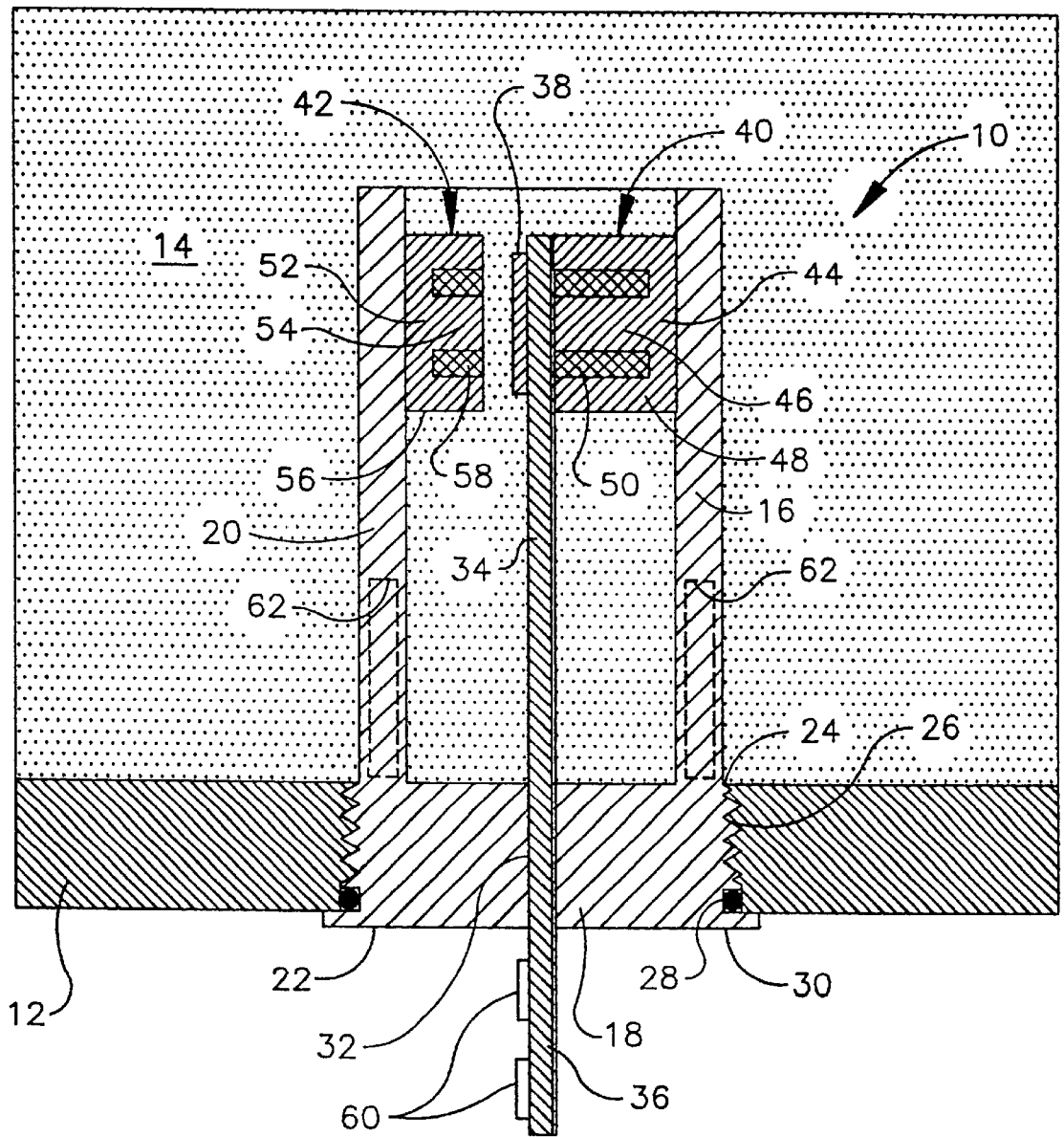
FIG. 1 a is cross-section view of a ferromagnetic particle sensor.

Referring initially to FIG. 1, a ferromagnetic particle sensor is shown and generally designated 10. FIG. 1 shows that the ferromagnetic particle sensor is installed in the base of a lubricating fluid reservoir 12, e.g., the base of an engine oil pan. As shown, the ferromagnetic particle sensor 10 is completely submerged in lubricating fluid 14.

FIG. 1 shows an exemplary, non-limiting embodiment of the ferromagnetic particle sensor 10. The exemplary sensor 10 can include a generally cylindrical housing 16 which extends into the fluid reservoir 12. The housing 16 includes a base 18 with a continuous cylindrical sidewall 20 extending therefrom. A flange 22 extends radially from the bottom end of the base 18 and abuts the exterior surface of the fluid reservoir 12 when the sensor 10 is properly installed therein. As shown in FIG. 1, the base 18 of the housing 16 is formed with external threads 24 above the flange 22. The external threads 24 formed by the housing 16 engage correspondingly sized and shaped internal threads 26 formed by the fluid reservoir 12. FIG. 1 further shows an "O" ring groove 28 that circumscribes the base 18 of the housing 16 immediately adjacent to the flange 22. An "O" ring 30 is disposed within the groove 28 in order to seal the junction between the sensor 10 and the reservoir 12 when the sensor 10 is threaded therein.

As shown in FIG. 1, a printed circuit board 32 can be installed in the center of the base 18. FIG. 1 shows that the circuit board 32 can include an internal portion 34 that extends into the housing 16 such that it is submerged in the fluid 14. The circuit board 32 can also include an external portion 36 that extends through the base 18 beyond the flange 22. As further shown, a mass sensitive surface acoustic wave (SAW) sensor 38 can be mounted on the internal portion 34 of the circuit board 32 near the end thereof.

FIG. 1 shows that the preferred ferromagnetic particle sensor 10 further includes a generally cylindrical first electromagnet 40 and a generally cylindrical second electromagnet 42. As shown, the first electromagnet 40 includes a core structure 44 that includes a center pole 46 and an outer ring 48. A wire is wound around the center pole 46 of the core 44 to form a generally toroidal coil 50. Similarly, the second electromagnet 42 includes a core 52 that has a center pole 54 and an outer ring 56. Like the first electromagnet 40, a wire is wound around the center pole 54 to form a generally toroidal coil 58. In a preferred embodiment, the core 46, 52 of each electromagnet 40, 42 is made from a soft magnetic material in order to prevent any residual magnetism in the core from attracting particles other than during the sample period, as described below.

As shown in FIG. 1, the first electromagnet 40 is attached to the inner surface of the continuous sidewall 20 such that the center pole 46 of the core 44 is directly behind the SAW sensor 38. FIG. 1 shows that the first electromagnet 40 is supported by the circuit board 32 and the continuous sidewall 20. On the other hand, the second electromagnet 42 is attached to the inner surface of the continuous sidewall 20 such that the center pole 54 is directly in front of, and slightly spaced from, the SAW sensor 38.

As further shown in FIG. 1, processing electronics 60 are attached to the external portion 36 of the printed circuit board 32. FIG. 1 also shows that the continuous sidewall 20 of the housing 16 is formed with plural holes 62 there through. The holes 62 allow fluid 14 to flow through the housing 16 during testing.

Figure 2:
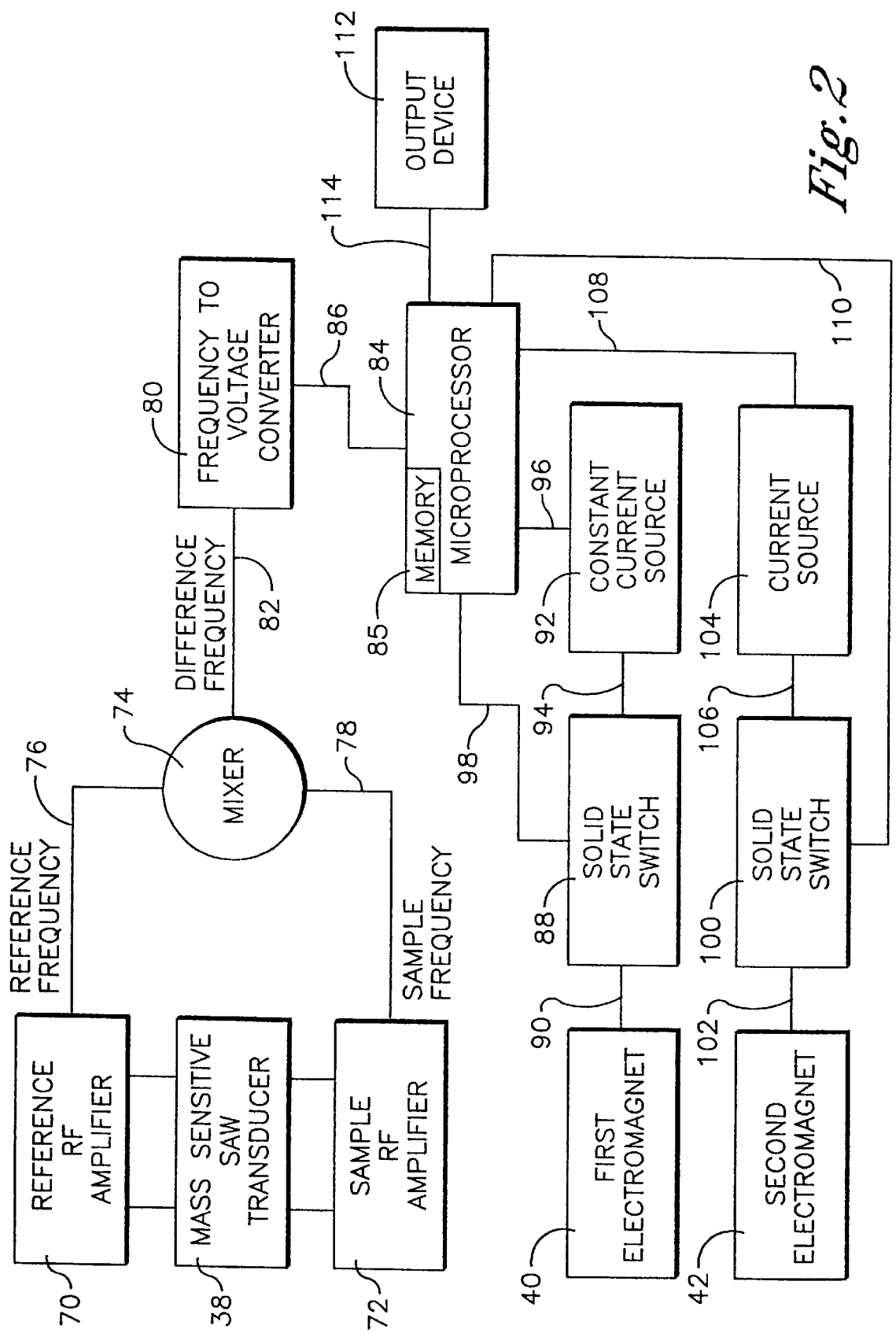
FIG. 2 is a block diagram of the ferromagnetic particle sensor.

Referring now to FIG. 2, a block diagram of the particle sensor is shown. FIG. 2 shows that the mass sensitive SAW transducer 38 includes a reference radio frequency (RF) amplifier 70 and a sample RF amplifier 72. The reference RF amplifier outputs a reference frequency to a mixer 74 via electrical line 76. Moreover, the sample RF amplifier 72 outputs a sample frequency to the mixer 74 via electrical line 78. In turn, the mixer 74 outputs a difference frequency, i.e., the difference between the reference frequency and the sample frequency, to a frequency-to-voltage converter 80 via electrical line 82.

The converter 80 is connected to a microprocessor 84 via electrical line 86 and outputs a voltage signal thereto representing the mass of a particle inducing a force on the SAW transducer 38. As shown, the microprocessor 84 includes a memory 85. FIG. 2 shows that the first electromagnet 40 is connected to a first switch 88, e.g., a first solid state switch, via electrical line 90. The first switch 80 is connected to a constant current source 92 via electrical line 94 which provides constant current to the first electromagnet 40 when the first switch 88 is opened. The constant current source 92, in turn, is connected to the microprocessor 84 via electrical line 96. As shown in FIG. 2, the first switch 88 is also connected to the microprocessor 84 via electrical line 98 through which the microprocessor 84 sends a control signal to open or close the first switch 88.

FIG. 2 further shows that the second electromagnet 42 is connected to a second switch 100, e.g., a second solid state switch, via electrical line 102. The second switch 100 is connected to a current source 104 via electrical line 106 which provides current to the second electromagnet 42 when the second switch 100 is opened. The current source 104, in turn, is connected to the microprocessor 84 via electrical line 108. As shown in FIG. 2, the second switch 100 is also connected to the microprocessor 84 via electrical line 110 through which the microprocessor 84 sends a control signal to open or close the second switch 100. FIG. 2 also shows an output device 112 connected to the microprocessor 84 via electrical line 114.

In a preferred embodiment, the microprocessor 84 is an appropriate circuit or chip incorporated into the processing electronics 60 that are attached to the circuit board 32. However, it is to be understood that the microprocessor 84 can be, e.g., an engine control module (ECM), a body control module (BCM), a powertrain control module (PCM), or any similar device. Moreover, it is to be understood that the output device 112 can be an audible warning device, e.g., a buzzer or audible alarm. The output device 112 can also be a visual warning device, e.g., a warning lamp or other visual display. Or, the output device 112 can be a visual indicator of the wear metal content in the lubricating fluid 14.

Operation

It is to be understood that the microprocessor 84 controls the entire measurement cycle. The RF amplifiers 70, 72 and SAW transducer 38 form two oscillators. The signals therefrom are fed into the mixer 74 which outputs a signal that represents the difference between the two frequencies output by the RF amplifiers 70, 72. The difference signal is input into a frequency to voltage converter and the direct current (DC) output is fed into the microprocessor 84.

To measure for wear metals, first, the difference frequency value with the electromagnets 40, 42 de-energized is stored in the memory 85 of the microprocessor 84. Then, the first electromagnet 40 is energized with a high current level and the difference frequency is monitored. When less than a one-tenth percent (0.1%) change in frequency in a predetermined time is measured, the current to the first electromagnet 40 is switched to the constant current mode. The value of the difference frequency with the constant current applied to the first electromagnet 40 is then averaged over multiple readings and stored. The microprocessor 40 then switches the first electromagnet 40 to a degauss cycle, i.e., a decreasing amplitude AC current is provided thereto, to demagnetize the magnetic core 44 and any ferromagnetic particles within the measurement area. At the same time, the second electromagnet 42 is energized to attract any ferromagnetic particles away from the SAW transducer 38.

When the value of the difference frequency matches or is within one-hundredth of a percent (0.01%) of the start value the current to the second electromagnet 42 is switched to a decreasing amplitude AC current to degauss the core 52 and any local ferromagnetic particles. Particles that are demagnetized will not group together or stick to any ferrous surfaces due to magnetic attraction. If the difference frequency does not return to the start value, the cycle to remove particles will be repeated for a maximum of two more times or until the difference frequency meets the start specifications. If the difference frequency does not match the start value thereof, a new value for the difference frequency will be stored.

It is to be understood that the microprocessor 84 calculates the slope of the data points collected. The microprocessor 84 monitors the slope of the data points to determine if a significant change in slope, indicative of increased wear, occurs. If the microprocessor 84 does detect an increase in wear rate, it outputs a signal to the output device 112 to warn the driver.

With the configuration of structure described above, it is to be appreciated that the ferromagnetic particle sensor 10 provides a means for determining the quantity of wear metals in lubricating fluid 14, e.g., oil in an engine. Thus, the need for processing a fluid sample in a laboratory is obviated.

While the particular FERROMAGNETIC PARTICLE SENSOR as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

What is claimed is:

1. A method for measuring ferromagnetic particles in lubricating fluid having moving parts therein, comprising the acts of:

providing at least a first electromagnet;

providing at least a second electromagnet;

disposing a mass sensitive surface acoustic wave sensor therebetween, the mass sensitive surface acoustic wave sensor including a reference radio frequency amplifier outputting a reference frequency and a sample radio frequency amplifier outputting a sample frequency;

determining a difference frequency at least partially based on the reference frequency and the sample frequency; and at least partially based on the difference frequency, determining a wear rate of the parts disposed in the lubricating fluid.

2. The method of claim 1 further comprising the act of:

at least partially based on the wear rate, indicating that the lubricating fluid needs to be changed.

* * * * *